United States Patent [19]
Elliott et al.

[11] Patent Number: 5,037,850
[45] Date of Patent: Aug. 6, 1991

[54] SKIN TREATMENT COMPOSITIONS

[75] Inventors: Thomas J. Elliott, London; Elspeth A. Murrell, Surrey, both of England

[73] Assignee: Beecham Group p.l.c., England

[21] Appl. No.: 418,248

[22] Filed: Oct. 6, 1989

Related U.S. Application Data

[63] Continuation of Ser. No. 84,127, Aug. 12, 1987, abandoned, which is a continuation of Ser. No. 494,129, May 13, 1983, abandoned.

[30] Foreign Application Priority Data

May 15, 1982 [GB] United Kingdom ............... 8214201

[51] Int. Cl.$^5$ ........................................... A61K 31/215
[52] U.S. Cl. ..................................... 514/529; 514/725
[58] Field of Search ........................ 814/529; 514/725

[56] References Cited

U.S. PATENT DOCUMENTS 4,333,924 6/1988 Bowley et al. .................. 424/170

FOREIGN PATENT DOCUMENTS 2019839 4/1970 Fed. Rep. of Germany .
1452791 8/1965 France .
1487543 5/1976 United Kingdom .

OTHER PUBLICATIONS

Chemical Abstracts, 88:55084c (1978).
Chemical Abstracts, 86:83499u (1977).
Sporn et al, Nature, vol. 263, Sep. 9, 1976, pp. 110-113.

Primary Examiner—Leonard Schenkman
Attorney, Agent, or Firm—Rosenman & Colin

[57] ABSTRACT

A skin-care composition comprising a topically acceptable oil-in-water or water-in-oil emulsion base and from 1,000 to 15,000 I Ug$^{-1}$ of a $C_{1-10}$ alkyl ether or a $C_{3-10}$ alkyl ester of retinol is disclosed. The composition preferably contains an anti-oxidant such as butylated hydroxytoluene or butylated hydroxyanisole. The composition is useful in promoting epidermal mitosis.

20 Claims, No Drawings

SKIN TREATMENT COMPOSITIONS

CROSS-REFERENCE

This is a continuation of Ser. No. 084,127 filed Aug. 12, 1987 which is a continuation of Ser. No. 494,129 filed May 13, 1983 both abandoned.

This invention relates to topical compositions containing esters or ethers of retinol which are useful in the care of skin.

British Patent Specification No. 1,489,133 describes and claims a liquid, semi-liquid or gel composition comprising a topically acceptable oil-in-water or water-in-oil emulsion base and retinol acetate in an amount from 1,000 to 15,000 IUg$^{-1}$. Such compositions are of value in promoting epidermal mitosis and thus lead to a desirable thickening or αplumpingα effect on the skin.

Published British Patent Application No. 2,026,319 describes and claims a similar composition to that of Specification No. 1,489,133, wherein the formulation of the emulsion base leads to high activity in skin thickening.

Although the compositions disclosed in the above two patent specifications give an enhanced skin thickening effect, the retinol acetate tends to decompose over a period of time, hence reducing the shelf life of the product. The decomposition is due largely to hydrolysis of the acetate by water in the emulsion base, followed by rapid oxidation of the free retinol. Furthermore, since retinol acetate is water insoluble it is normally mixed with a non-ionic surfactant, thereby forming a water soluble form, prior to incorporation into the emulsion base.

It has now been found that acceptable levels of skin thickening coupled with good stability can be obtained if a $C_{1-10}$-alkyl ether or a $C_{3-10}$-alkyl ester of retinol is used in place of retinol acetate. It has also been found that the $C_{1-10}$ ether or $C_{3-10}$ ester of retinol may be incorporated into an emulsion base either as a water soluble or water insoluble form.

Accordingly, the present invention provides a skin-care composition, comprising a topically acceptable oil-in-water or water-in-oil emulsion base and from 1,000 to 15,000 I Ug$^{-1}$ of a $C_{3-10}$ alkyl ester or a $C_{1-10}$ alkyl ether of retinol.

Preferably, the composition of the invention comprises the all trans- isomer of a $C_{1-10}$ alkyl ether or a $C_{3-10}$ alkyl ester of retinol.

Preferably, the composition comprises a $C_{3-7}$ straight chain, branched chain, or cyclo- alkyl ester of retinol; for example retinol propionate, butyrate, cyclopentanecarboxylate, pivalate, valerate, hexanoate, and heptanoate.

Preferred ethers of retinol for use in the composition of the invention are $C_{1-7}$ alkyl ethers, suitably the methyl ether of retinol is used.

Preferably, the composition comprises from 1,000 to 10,000 I Ug$^{-1}$, or more suitably from 2,000 to 5,000 I Ug$^{-1}$ of a $C_{1-10}$ alkyl ether or a $C_{3-10}$ alkyl ester of retinol.

The preferred emulsion base is an oil-in-water emulsion base containing from 20 to 40% by weight of oil.

An emulsifier is preferably used in the composition of the invention, and this may be an anionic, cationic or non-ionic type. In order of their ability to produce a skin thickening effect, anionic emulsifiers are less effective than non-ionic emulsifiers which are in turn less effective than cationic emulsifiers. However, the latter can cause skin irritation when used, and non-ionic emulsifiers are, therefore, preferred.

It has been found that the proportion of non-ionic emulsifier in the compositions of the invention is not critical, but at least 1% by weight is preferred to give a stable emulsion. Suitably an amount in the range 2% to 12%, more suitably 4% to 8% is preferred.

Examples of oils suitable for inclusion in the present compositions include: volatile linear iso-paraffins, acyclic dimethylpoly siloxanes, cyclic dimethylpoly siloxanes, mineral oils, vegetable oils, synthetic fatty acid esters, fatty alcohols, lanolin and its derivatives.

Examples of non-ionic emulsifiers suitable for inclusion in the present compositions include: sorbitan monostearate, glyceryl monostearate, polysorbates, polyethylene derivatives of fatty alcohols.

The compositions of this invention should desirably include an anti-oxidant effective in preventing oxidation of the retinol component and consequent reduction in the activity of the composition. Some anti-oxidants are effective in this respect but themselves oxidise to give a noticeable yellowing of the cream.

Two anti-oxidants which are particularly suitable for incorporation are butylated hydroxytoluene (BHT), (2,6-di-tert-butyl-p-cresol) and butylated hydroxyanisole (BHA), (2-tert-butyl-4-hydroxyanisole or 3-tert-butyl-4- hydroxyanisole) or a mixture of these. Accordingly in another of its aspects, the invention includes a composition in accordance with the invention including BHT and/or BHA as anti-oxidant.

The retinol component of the compositions may be dispersed in the emulsion in the form of a 'solubilised' mixture. Such mixtures are generally solutions of the retinol component in hydrophilic organic solvents such as glycerine and/or propylene glycol, together with a surfactant such as Tween 80.

The invention also provides a process for preparing a skin-care composition comprising a topically acceptable oil-in-water or water-in-oil emulsion base and from 1,000 to 15,000 I Ug$^{-1}$ of a $C_{3-10}$ alkyl ester or a $C_{1-10}$ alkyl ether of retinol, which comprises mixing the emulsion base with the retinol component.

Preferably, the retinol component is added to the emulsion base with stirring at a temperature of less than 50° C., suitably 35° C.

The $C_{1-10}$ alkyl ethers and $C_{3-10}$ alkyl esters of retinol are known compounds or can be prepared by procedures analogous to known preparative procedures.

The present invention further provides a method of treatment of the skin of the human or animal body, comprising the topical application of a skin-care composition of the present invention.

The following are examples of compositions in accordance with the invention.

Example 1

| Formulation | % w/w |
| --- | --- |
| Sorbitan stearate | 2.00 |
| Polysorbate 60 | 2.00 |
| Cetyl alcohol | 2.00 |
| Cetyl alcohol/PEG 40 Castor Oil | 2.50 |
| Mineral Oil | 25.00 |
| Lanolin | 2.50 |
| Decyl oleate | 2.00 |
| Preservatives | 0.37 |
| Anti-oxidant (BHT) | 0.20 |
| Perfume | 0.45 |
| Water soluble retinol propionate | 3,000–7,000 IU/g |

-continued

Example 1

| Formulation | % w/w |
|---|---|
| Deionised water to | 100.00 |

Sorbiton stearate, polysorbate 60, cetyl alcohol, PEG 40 caster oil, mineral oil, lanolin, decyl oleate, anti-oxidant, and preservatives were blended together and heated to about 78° C. The mixture was added to water at 78° C. with stirring. The mixture was homogenised then allowed to cool to 35° C.

Retinol propionate was added to the mixture with stirring. The mixture was again homogenised, then cooled to 25° C. Perfume was added with stirring.

The following Examples were prepared using a procedure analogous to that used in Example 1.

Example 2

| | % w/w |
|---|---|
| Glyceryl stearate/PEG 100 Stearate | 4.50 |
| Cetostearyl alcohol | 4.50 |
| Cetearyl octanoate | 3.00 |
| Stearyl heptanoate | 2.00 |
| Fatty acid ester of propylene glycol | 4.00 |
| Mineral oil/lanolin alcohol | 3.00 |
| Octyl palmitate | 5.00 |
| Mineral oil | 5.00 |
| Antioxidant (BHT) | 0.20 |
| Propylene glycol | 3.00 |
| Preservatives | 0.62 |
| Perfume | 0.20 |
| Water soluble retinol cyclopentanoate | 3,000–7,000 IU/g |
| Deionised water to | 100.00 |

Example 3

| | % w/w |
|---|---|
| Ceteareth 12 | 2.00 |
| Cetyl alcohol | 8.00 |
| Squalane | 10.00 |
| Antioxidant (BHT) | 0.20 |
| Propylene glycol | 2.00 |
| Preservatives | 0.37 |
| Perfume | 0.30 |
| Oil soluble retinol methyl ether | 3,000–7,000 IU/g |
| Deionised water to | 100.00 |

Example 4

| | % w/w |
|---|---|
| Sorbitan stearate | 1.50 |
| Polysorbate 60 | 2.00 |
| Glyceryl stearate | 4.00 |
| Cetyl alcohol | 2.00 |
| Octyl palmitate | 3.00 |
| Mineral oil | 8.00 |
| Decyl oleate | 3.00 |
| Anti-oxidant (BHT) | 0.10 |
| Polyethylene microspheres | 3.00 |
| Glycerine | 5.00 |
| Allantoin | 0.10 |
| Propylene glycol | 3.00 |
| Preservatives | 0.35 |
| Oil soluble retinol heptanoate | 3,000–7,000 IU/g |
| Perfume | 0.20 |
| Deionised water to | 100.00 |

What is claimed is:

1. A skin care composition, which comprises a topically acceptable oil-in-water or water-in-oil emulsion base and from 1,000 to 15,000 IUg$^{-1}$ of a $C_{3-10}$ alkanoyl ester of retinol.

2. A composition as claimed in claim 1, wherein the retinol component is the all trans-isomer.

3. A composition as claimed in claim 1, wherein the amount of the retinol ester is from 1,000 to 10,000 I Ug$^{-1}$.

4. A composition as claimed in claim 3 wherein the amount of the retinol ester is from 2,000 to 5,000 I Ug$^{-1}$.

5. A composition as claimed in claim 1, wherein the emulsion base comprises from 20 to 40% by weight of oil.

6. A composition as claimed in claim 1, including an emulsifying agent.

7. A composition as claimed in claim 6, wherein at least 1% by weight of the composition of a nonionic emulsifying agent is present.

8. A composition as claimed in claim 1, including an anti-oxidant.

9. A composition as claimed in claim 8, wherein the anti-oxidant is butylated hydroxytoluene or is butylated hydroxyanisole.

10. A skin care composition, which comprises a topically acceptable oil-in-water or water-in-oil emulsion base and from 1,000 to 15,000 I Ug$^{-1}$ of a retinol ester selected from the group consisting of retinol propionate, retinol butyrate, retinol cyclopentanecarboxylate, retinol pivalate, retinol valerate, retinol hexanoate and retinol heptanoate.

11. A method of treatment of the skin of the animal or human body to obtain enhanced skin thickening, which comprises topically applying an effective amount on the body of the animal or human of a skin care composition comprising a topically acceptable oil-in-water or water-in-oil emulsion base and from 1,000 to 15,000 IUg$^{-1}$ of a $C_{3-10}$ alkanoyl ester of retinol.

12. A method as claimed in claim 11, wherein the retinol component is the all trans-isomer.

13. A method as claimed in claim 11, wherein the amount of the retinol ester is from 1,000 to 10,000 I Ug$^{-1}$.

14. A method as claimed in claim 13, wherein the amount of the retinol ester is from 2,000 to 5,000 I Ug$^{-1}$.

15. A method as claimed in claim 11, wherein the emulsion base comprises from 20 to 40 by weight of oil.

16. A method ad claimed in claim 11, including an emulsifying agent.

17. A method as claimed in claim 16, wherein at least 1% by weight of the composition of a nonionic emulsifying agent is present.

18. A method as claimed in claim 11, including an anti-oxidant.

19. A method as claimed in claim 18, wherein the anti-oxidant is butylated hydroxytoluene or is butylated hydroxyanisole.

20. A method as claimed in claim 11, wherein the retinol ester is selected from the group consisting of retinol propionate, retinol butyrate, retinol cyclopentanecarboxylate, retinol pivalate, retinol varerate, retinol hexanoate and retinol heptanoate.

* * * * *